US007744897B2

(12) United States Patent
Dillon et al.

(10) Patent No.: US 7,744,897 B2
(45) Date of Patent: Jun. 29, 2010

(54) HUMAN IMMUNODEFICIENCY VIRUS GP41 MIMETIBODY POLYPEPTIDES

(76) Inventors: Susan B. Dillon, 10 Fieldstone La., Bryn Mawr, PA (US) 19010; Alfred Michael Del Vecchio, 109 Turnhill Ct., West Chester, PA (US) 19380; Chichi Huang, 69 Highpoint Dr., Berwyn, PA (US) 19312; Karyn T. O'Neil, 222 Kirkbrae Rd., Kennett Square, PA (US) 19348; Robert T. Sarisky, 2569 Cold Spring Rd., Lansdale, PA (US) 19446

( * ) Notice: Subject to any disclaimer, the term of this patent is extended or adjusted under 35 U.S.C. 154(b) by 771 days.

(21) Appl. No.: 11/018,102

(22) Filed: Dec. 21, 2004

(65) Prior Publication Data
US 2005/0136061 A1    Jun. 23, 2005

Related U.S. Application Data

(60) Provisional application No. 60/532,291, filed on Dec. 23, 2003.

(51) Int. Cl.
*A61K 39/00* (2006.01)
*A61K 30/21* (2006.01)
*C12N 5/00* (2006.01)
(52) U.S. Cl. .................. 424/188.1; 424/208.1; 435/325
(58) Field of Classification Search .............. 424/188.1, 424/192.1, 208.1; 530/350
See application file for complete search history.

(56) References Cited

U.S. PATENT DOCUMENTS

| 5,817,767 A | 10/1998 | Allaway et al. |
| 2004/0171542 A1* | 9/2004 | Bailon et al. .................. 514/12 |

FOREIGN PATENT DOCUMENTS

| WO | WO 94/02505 A1 | 2/1994 |
| WO | WO 94/28920 A1 | 12/1994 |
| WO | WO 96/19495 A1 | 6/1996 |
| WO | WO 99/59615 A1 | 11/1999 |
| WO | WO 01/03723 A1 | 1/2001 |
| WO | WO 01/51673 A1 | 7/2001 |
| WO | WO 01/07081 A | 2/2002 |
| WO | WO 02/103026 A2 | 12/2002 |
| WO | WO 03/016333 A | 2/2003 |
| WO | WO 03/066078 A1 | 8/2003 |
| WO | WO 03/084477 A2 | 10/2003 |
| WO | WO 2004/002424 A2 * | 1/2004 |
| WO | WO2004/029074 A2 | 4/2004 |
| WO | WO2004/029074 A3 | 4/2004 |
| WO | WO 2004/106364 A1 | 12/2004 |

OTHER PUBLICATIONS

Frazer, J. K., and J. D. Capra, 1999, "Immunoglobulins: Structure and Function", in Fundamental Immunology, Fourth Edition, W. E. Paul, ed., Lippincott-Raven Publishers, Philadelphia, pp. 41, 43, 44, 46-49, and 54.*

Max, E. E., 1999, "Immunoglobulins: Molecular Genetics", in Fundamental Immunology, Fourth Edition, W. E. Paul, ed., Lippincott-Raven Publishers, Philadelphia, pp. 142-143.*
Braren, I., et al., 2007, "Comparative expression of different antibody formats in mammalian cells and *Pichia pastoris*", Biotechnol. Appl. Biochem. 47:205-214.*
Geng, S., et al., 2007, "Human IgG1 Cgamma1 domain is crucial for the bioactivity of the engineered anti-CD20 antobidies", Cell. Mol. Immunol. 4(2):121-125.*
Gallaher, et al., "A General Model for the Transmembrane Proteins of HIV and Other Retroviruses," *AIDS Research and Human Retroviruses*, 5(4): 431-440 (1989).
Delwart, et al., "Retroviral Envelope Glycoproteins Contain a "Leucine Zipper"-like Repeat," *AIDS Research and Human Retroviruses*, 6(6): 703-706 (1990).
Wild, et al., "A Synthetic Peptide from HIV-1 gp41 is a Potent Inhibitor of Virus-Mediated Cell-Cell Fusion," *AIDS Research and Human Retroviruses*, 9(11): 1051-1053 (1993).
Dubay, et al., "Mutations in the Leucine Zipper of the Human Immunodeficiency Virus Type 1 Transmembrane Glycoprotein Affect Fusion and Infectivity," *Journal of Virology*, 66(8): 4748-4756 (1992).
Jiang, et al., "Peptide and Non-peptide HIV Fusion Inhibitors," *Current Pharmaceutical Design*, 8: 563-580 (2002).
Dragic, et al., "HIV-1 entry into CD4+ cells is mediated by the chemokine receptor CC-CKR-5," *Nature*, 381: 667-673 (1996).
Deng, et al., "Identification of a major co-receptor for primary isolates of HIV-1," *Nature*, 381: 661-666 (1996).
Feng, et al., "HIV-1 Entry Cofactor: Functional cDNA Cloning of a Seven-Transmembrane G Protein-Coupled Receptor," *Science*, 272: 872-877 (1996).
Eron, et al., "Entry and Fusion Inhibitors: an Update," *The PRN Notebook*, 7(1): 16-22 (2002).
Kilby, et al., "Novel therapies Based on Mechanisms of HIV-1 Cell Entry," *New England Journal of Medicine*, 348(22): 2228-2238 (2003).
Eron, et al., "Short-Term Safety and Antiretroviral Activity of T-1249, a Second-Generation Fusion Inhibitor of HIV," *JID*, 189: 1075-1083 (2004).
Tan, et al., "Atomic structure of a thermostable subdomain of HIA-1 gp41," *Proceedings of the National Academy of Science USA*, 94: 12303-12308 (1997).
Weissenhorn, et al., "Atomic structure of the ectodomain from HIV-1 gp41," *Nature*, 387: 426-430 (1997).
Chan, et al., "Core Structure of gp41 from the HIV Envelope Glycoprotein," *Cell*, 89: 263-273 (1997).
Wild, et al., "Propensity for a leucine zipper-like domain of human immunodeficiency virus type 1 gp41 to form oligomers correlates with a role in virus-induced fusion rather than assembly of the glycoprotein complex," *Proceedings of the National Academy of Science USA*, 91: 12676-12680 (1994).
Kilby, et al., "Potent suppression of HIV-1 replication in humans by T-20, a peptide inhibitor of gp41-mediated virus entry," *Nature Medicine*, 4(11): 1302-1307 (1998).
PCT International Search Report dated Jun. 21, 2005.
Supplementary EP Search Report dated Sep. 25, 2007.
Ruprecht, et al., "Antibody protection: passive immunization of neonates against oral AIDS virus challenge," 21: 3370-3373 (2003).

* cited by examiner

*Primary Examiner*—Jeffrey S. Parkin
(74) *Attorney, Agent, or Firm*—Kirk Baumeister (57) ABSTRACT

HIV gp41 mimetibody polypeptides and encoding polynucleotides are disclosed. Methods of utilizing the polypeptides to reduce or inhibit HIV fusion with a cell membrane and entry into target cells are also disclosed.

6 Claims, 1 Drawing Sheet

HUMAN IMMUNODEFICIENCY VIRUS GP41 MIMETIBODY POLYPEPTIDES

CROSS-REFERENCE TO RELATED APPLICATION

This application claims the benefit of U.S. Provisional Application No. 60/532,291, filed Dec. 23, 2003.

FIELD OF THE INVENTION

The present invention relates to anti-retroviral agents, in particular human immunodeficiency virus gp41 mimetibodies and their use as therapeutics.

BACKGROUND OF THE INVENTION

Infection with human immunodeficiency virus type 1 (HIV-1), the lentivirus that causes acquired immunodeficiency syndrome (AIDS), is one of the leading causes of death worldwide. Most currently available antiretroviral agents inhibit essential HIV-1 enzymes, either the reverse transcriptase or the protease. Recent advances have markedly improved the outcome for many patients who receive these classes of antiretroviral drugs. However, the success of current therapy is limited by the emergence of drug-resistant viruses, the necessity of sustained adherence to complex regimens and the potential for toxic side effects. Novel classes of safe and effective agents with a low risk of cross-reactivity with other antiretroviral drugs continue to be needed.

It is thought that targeting viral entry may have advantages over the inhibition of steps in the viral life cycle after the cell has been infected (reviewed in Kilby and Eron, *N. Engl. J. Med.* 348: 2228-2238 (2003)). The HIV-1 envelope glycoprotein is involved in viral entry and consists of two noncovalently associated subunits, a surface glycoprotein (gp120) and a transmembrane glycoprotein (gp41). Portions of gp120 bind to the CD4 receptor and chemokine coreceptors (CXCR4 and CCR5) on target cells (Feng et al., *Science* 272: 872-877 (1996); Dragic et al., *Nature* 381: 667-673 (1996); Deng et al., *Nature* 381: 661-666 (1996)). After gp120-CD4-coreceptor binding, the gp41 subunit undergoes a conformational change that promotes fusion of the viral and cellular membrane, resulting in entry of the viral core into the cell, transport to the nucleus and ultimately, proviral integration and expression (Chan et al., *Cell* 89: 263-273 (1997)).

The primary amino acid sequence of gp41 includes "heptad-repeat" regions (HR1 and HR2), reflecting the presence of periodic hydrophobic regions found in alpha-helical "coiled-coil" secondary structures (Gallaher et al., *AIDS Res. Hum. Retroviruses* 5: 431-440 (1989); Delwart et al., *AIDS Res. Hum. Retroviruses* 6: 703-706 (1990)). HR1 and HR2 form a helical bundle containing three members (a trimer) of each domain (Chan et al., supra; Tan et al., *Proc. Natl. Acad. Sci.* (*USA*) 94: 12303-12308 (1997); Weissenhorn et al., *Nature* 387: 426-430 (1997)). These heptad repeats have a role in the conformational changes essential for membrane fusion of HIV-1 with host cells (Dubay et al., *J. Virol.* 66: 4748-4756 (1992); Wild et al., *Proc. Natl. Acad. Sci.* (*USA*) 91: 12676-12680 (1994)).

Synthetic peptides that mimic HR2 segments of gp41 block fusion and have significant antiretroviral effects (Gallaher et al., supra; Delwart et al., supra; Dubay et al., *J. Virol.* 66: 4748-4756 (1992)). Two peptides, T-20 and T-1249, have been studied in clinical trials (Wild et al., *AIDS Res. Hum. Retroviruses* 9: 1051-1053 (1993); Eron et al., *J. Infect. Dis.* 189: 1075-1083 (2004); reviewed in Kilby and Eron, supra; also reviewed in Jiang et al., *Curr. Pharm. Des.* 8: 563-580 (2002)).

T-20 (FUZEON® brand of enfuvirtide), a 36-amino-acid peptide derived from the HR2 sequence, has been demonstrated to reduce viral levels in infected patients 1-2 logs in clinical trials (Kilby et al., *Nat. Med.* 4: 1302-1307 (1998)). This compound is used in combination with existing therapies employing multiple anti-HIV drugs such as highly active anti-retroviral therapy (HAART) and is also used to treat salvage therapy cases, where patients are no longer responsive to their treatment regimen. However, this peptide HIV fusion inhibitor is sensitive to proteolytic digestion and therefore has a short plasma half-life of about 1.8 hours. Consequently, large doses (90 mg/injection) need to be administered twice daily for full efficacy (reviewed in Jiang et al., supra).

In comparison, T-1249, a 39-amino-acid consensus peptide derived from HIV-1, HIV-2 and Simian Immunodeficiency Virus (SIV) gp-41, has an increased, but still relatively short plasma half-life of 9 to 14 hours and also needs to be injected twice daily to sustain effective blood levels (Eron and Hogan, *PRN Notebook* 7: 16-22 (2002)). Thus, a need exists for improved HIV fusion inhibitors with longer half-lives.

BRIEF DESCRIPTION OF THE DRAWINGS

FIG. 1 shows the inhibition of HIV infection of MT4-Luc cells by T-1249 peptide (FIG. 1A) and T-1249 mimetibody (FIG. 1B). Experiments were conducted as described in Example 2. RLU is a measure of luminescence. The ordinate units are log [T-1249 peptide], nM and log[MMB1249], nM, in FIGS. 1A and 1B, respectively.

SUMMARY OF THE INVENTION

One aspect of the invention is a polypeptide having the generic formula (II):

$$(V1\text{-}gp\text{-}Lk\text{-}V2\text{-}Hg\text{-}C_H2\text{-}C_H3)_{(t)} \qquad (II)$$

where V1 is a portion of an N-terminus of an immunoglobulin variable region, gp is a HIV gp41-derived peptide sequence, Lk is a polypeptide or chemical linkage, V2 is a portion of a C-terminus of an immunoglobulin variable region, Hg is at least a portion of an immunoglobulin variable hinge region, $C_H2$ is an immunoglobulin heavy chain $C_H2$ constant region and $C_H3$ is an immunoglobulin heavy chain $C_H3$ constant region and t is independently an integer from 1 to 10.

Another aspect of the invention is a polypeptide according to Formula (III):

$$(gp\text{-}Lk\text{-}V2\text{-}Hg\text{-}C_H2\text{-}C_H3)_{(t)} \qquad (III)$$

where gp is a human immunodeficiency virus (HIV) gp41-derived peptide sequence, Lk is a polypeptide or chemical linkage, V2 is a portion of a C-terminus of an immunoglobulin variable region, Hg is at least a portion of an immunoglobulin variable hinge region, $C_H2$ is an immunoglobulin heavy chain $C_H2$ constant region and $C_H3$ is an immunoglobulin heavy chain $C_H3$ constant region and t is independently an integer from 1 to 10.

Another aspect of the invention is a polypeptide according to Formula (IV):

$$(Hg\text{-}C_H2\text{-}C_H3\text{-}Lk\text{-}gp)_{(t)} \qquad (IV)$$

where gp is a human immunodeficiency virus (HIV) gp41-derived peptide sequence, Lk is a polypeptide or chemical linkage, V2 is a portion of a C-terminus of an immunoglobulin variable region, Hg is at least a portion of an immunoglobulin variable hinge region, $C_H2$ is an immunoglobulin heavy chain $C_H2$ constant region and $C_H3$ is an immunoglobulin heavy chain $C_H3$ constant region and t is independently an integer from 1 to 10.

Another aspect of the invention is a polypeptide comprising the sequence shown in SEQ ID NO: 1.

Another aspect of the invention is a polynucleotide comprising the sequence shown in SEQ ID NO: 2 or a complementary sequence.

Another aspect of the invention is a polynucleotide encoding the amino acid sequence shown in SEQ ID NOs: 1, 5, 6, 7, 8, 9, 10, 11, 12 or 13.

Another aspect of the invention is a polynucleotide comprising a polynucleotide encoding the amino acid sequence shown in SEQ ID NO: 1.

Another aspect of the invention is a method of inhibiting HIV infection of a target cell comprising contacting the cell with an HIV gp41 mimetibody pharmaceutical composition.

Another aspect of the invention is a method of reducing the symptoms of, or treating at least one HIV infection related condition or disorder, comprising administering an HIV gp41 mimetibody pharmaceutical composition to a patient in need thereof.

DETAILED DESCRIPTION OF THE INVENTION

All publications, including but not limited to patents and patent applications, cited in this specification are herein incorporated by reference as though fully set forth. Single letter amino acid codes are used herein as understood by those skilled in the art. Numbering of amino acid residues in immunoglobulin constant regions is based on residue one being the N-terminal amino acid in a wild type IgG1 or IgG4 Fc domain.

The present invention provides polypeptides having the properties and activities of HIV gp41-derived peptides wherein the polypeptides also mimic different types of immunoglobulin molecules such as IgA, IgD, IgE, IgG, or IgM, and any subclass thereof, such as IgA1, IgA2, IgG1, IgG2, IgG3 or IgG4, or combinations thereof, hereinafter referred to as "HIV gp41 mimetibodies." The invention also provides nucleic acids encoding HIV gp41 mimetibodies, vectors containing these nucleic acids, host cells, compositions and methods of making and using HIV gp41 mimetibodies.

Mimetibody Polypeptides and Compositions

The present invention generally relates to mimetibody polypeptides having the generic formula (I):

where V1 is a portion of an N-terminus of an immunoglobulin variable region, Pep is a polypeptide having a desired biological property, Lk is a polypeptide or chemical linkage, V2 is a portion of a C-terminus of an immunoglobulin variable region, Hg is at least a portion of an immunoglobulin hinge region, $C_H2$ is an immunoglobulin heavy chain $C_H2$ constant region and $C_H3$ is an immunoglobulin heavy chain $C_H3$ constant region and t is independently an integer of 1 to 10. For example, Pep can be a polypeptide derived from any viral protein involved in host cell membrane fusion and viral entry that is capable of blocking the fusion of the virus with a host cell membrane.

More particularly, the present invention relates to HIV gp41 mimetibody polypeptides that are capable of blocking the fusion of virus with a host cell membrane. The polypeptides have the generic formula (II):

where V1 is a portion of an N-terminus of an immunoglobulin variable region, gp is a gp41-derived peptide sequence, Lk is a polypeptide or chemical linkage, V2 is a portion of a C-terminus of an immunoglobulin variable region, Hg is at least a portion of an immunoglobulin hinge region, $C_H2$ is an immunoglobulin heavy chain $C_H2$ constant region and $C_H3$ is an immunoglobulin heavy chain $C_H3$ constant region and t is independently an integer of 1 to 10.

As used herein, "gp41-derived peptide" encompasses peptides, including consensus peptides, which are derived from the HR2 domain of gp41 from any HIV or SIV isolate. An exemplary gp41-derived peptide is T-20 having the amino acid sequence shown in SEQ ID NO: 3. Another exemplary gp41-derived peptide is the peptide T-1249 having the amino acid sequence shown in SEQ ID NO: 4. Other gp41-derived peptides include peptides that can mimic the activities of T-20 or T-1249 to serve as competitive decoys for binding the HR1 and HR2 domains of gp41. These peptides can include T-20 or T-1249 homologs that have at least one amino acid substitution, deletions or insertions. Other exemplary gp41-derived peptides are shown in PCT International Publication Nos. WO94/02505, WO94/28920, WO96/19495, WO99/59615, WO01/03723, WO01/51673 and WO04/029074 and also include peptides of Formula (V):

$$YTX_1X_2IYX_3LLEX_4SQX_5QQEKNEQELLELDKWASLWX_6WF \quad (V)$$

where $X_1$ is S, G or N; $X_2$ is L, I or T; $X_3$ is S, N or T; $X_4$ is K, E or D; $X_5$ is T or N and $X_6$ is N, E or D.

In the polypeptides of the invention, V1 is a portion of an N-terminus of an immunoglobulin variable region. Exemplary V1 amino acid sequences include QIQ or QVQ.

In the polypeptides of the invention, the linker portion (Lk) provides structural flexibility by allowing the mimetibody to have alternative orientations and binding properties. Exemplary linkers include non-peptide chemical linkages or amino acids linked by peptide bonds, wherein the amino acids are selected from the 20 naturally occurring amino acids. The linker portion can include a majority of amino acids that are sterically unhindered, such as glycine, alanine and serine and include GS, GGGS (SEQ ID NO: 14), and GSGGGS (SEQ ID NO: 15), polymers of GS, GGGS and GSGGGS, or any combination thereof. Other exemplary linkers within the scope of the invention may be longer than 20 residues and may include residues other than glycine, alanine and serine.

In the polypeptides of the invention, V2 is a portion of a C-terminal domain of an immunoglobulin variable region such as a heavy chain variable region. An exemplary V2 amino acid sequence is GTLVTVSS (SEQ ID NO: 16).

In the polypeptides of the invention, Hg is at least a portion of the hinge domain of an immunoglobulin variable region such as a heavy chain variable region. Exemplary Hg amino acid sequences include EPKSCDKTHTCPPCP (SEQ ID NO: 17), EPKSADKTHTCPPCP (SEQ ID NO: 18), ESKYGPPCPSCP (SEQ ID NO: 19), ESKYGPPCPPCP (SEQ ID NO: 20) and CPPCP (SEQ ID NO: 21).

In the polypeptides of the invention, $C_H2$ is an immunoglobulin heavy chain $C_H2$ constant region. Exemplary $C_H2$ amino acid sequences include:

```
                                          (SEQ ID NO: 22)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAK,
```

```
                                                        (SEQ ID NO: 23)
APEAAGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAK, (SEQ ID NO: 24)
APEFLGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPS

SIEKTISKAK
and
                                                        (SEQ ID NO: 25)
APEAAGGPSVFLFPPKPKDTLMISRTPEVTCVVVDVSQEDPEVQFNWYVD

GVEVHNAKTKPREEQFNSTYRVVSVLTVLRQDWLNGKEYKCKVSNKGLPS

SIEKTISKAK.
```

In the polypeptides of the invention, $C_H3$ is an immunoglobulin heavy chain $C_H3$ constant region. Exemplary $C_H3$ amino acid sequences include:

GQPREPQVYTLPPSRDELTKNQVSLT-CLVKGFYPSDIAVEWESNGQPENNYKT-TPPVLDSDGSFFLYS KLTVDKSRWQQGNVFSCSVM-HEALHNHYTQKSLSLSPGK (SEQ ID NO: 26) and GQPREPQVYTLPPSQEEMTKNQVSLT-CLVKGFYPSDIAVEWESNGQPENNYKT-TPPVLDSDGSFFLYS RLTVDKSRWQEGNVFSCSVM-HEALHNHYTQKSLSLSLGK (SEQ ID NO: 27). It will be recognized by those skilled in the art that the $C_H3$ region of the polypeptides of the invention may have its C-terminal amino acid cleaved off when expressed in certain recombinant systems.

In the polypeptides of the invention, the FcRn scavenger receptor-binding site of the immunoglobulin molecules is preserved at the junction of the $C_H2$ and $C_H3$ region. Since FcRn binding enables the return of pinocytosed immunoglobulin back to the extracellular space, it is expected that the half-life of HIV gp41 mimetibodies will be significantly extended relative to T-20, T-1249 or other gp41-derived peptides.

In one embodiment, the polypeptides of the invention lack the V1 sequence at the N-terminal of the gp41-derived peptide. The polypeptides have the generic Formula III.

$$(gp-Lk-V2-Hg-C_H2-C_H3)_{(t)} \quad (III)$$

In another embodiment of the polypeptides of the invention, the gp41-derived peptide is linked to the C-terminus of the $C_H3$ domain as shown in Formula IV. In polypeptides of Formula IV, gp can also be D-amino acid-containing peptides as shown in U.S. Pat. Nos. 6,747,126 and 6,818,740.

$$(Hg-C_H2-C_H3-Lk-gp)_{(t)} \quad (IV)$$

In another embodiment of the polypeptides of the invention, a heterodimeric structure containing the monomer (V1-gp-Lk-V2-Hg-$C_H2$-$C_H3$) and the monomer (V1-Lk-V2-Hg-$C_H2$-$C_H3$) or the monomer (Hg-$C_H2$-$C_H3$-Lk-gp) can be formed through covalent linkages, such as a Cys-Cys disulfide bond in the hinge region.

One embodiment of the present invention is a polypeptide comprising a polypeptide according to formula (II) where V1 is QIQ, gp is a single copy of T-1249 (SEQ ID NO: 4), V2 is a J region of a naturally occurring IgG (SEQ ID NO: 16), Hg is a complete IgG1 hinge region (SEQ ID NO: 17), $C_H2$ and $C_H3$ are of the IgG1 isotype subclass (SEQ ID NOs: 22 and 26) and t is 2. The complete polypeptide sequence of the monomer form of this embodiment is shown in SEQ ID NO: 1.

Another embodiment of the present invention is a polypeptide comprising a polypeptide according to formula (II) where V1 is QIQ, gp is a single copy of T-20 (SEQ ID NO: 3), V2 is a J region of a naturally occurring IgG (SEQ ID NO: 16), Hg is a complete IgG1 hinge region (SEQ ID NO: 17), $C_H2$ and $C_H3$ are of the IgG1 isotype subclass (SEQ ID NOs: 22 and 26) and t is 2. The complete polypeptide sequence of the monomer form of this embodiment is shown in SEQ ID NO: 11.

In other embodiments of the present invention, the V1, V2, Hg, $C_H2$ and $C_H3$ are derived from those of an immunoglobulin isotype subclass other than IgG1, such as IgG4. IgG1 and IgG4 subclasses differ in the number of cysteines in the hinge region. Like the IgG1 subclass, there are two cysteines in the IgG4 hinge that participate in the disulfide bonding between heavy chains. However, the cysteine in IgG1 hinge that is normally involved in disulfide bonding to the light chain is absent in the IgG4 hinge. Therefore, the IgG4 hinge is less flexible than the IgG1 hinge.

In addition, the two isotypes differ in their ability to mediate complement dependent cytotoxicity (CDC) and antibody-dependent cellular cytotoxicity (ADCC). CDC is the lysing of a target in the presence of complement. The complement activation pathway is initiated by the binding of the first component of the complement system (C1q) to a molecule complexed with a cognate antigen. IgG1 is a strong inducer of the complement cascade and subsequent CDC activity, while IgG4 has little complement-inducing activity.

ADCC is a cell-mediated reaction in which cytotoxic cells that express Fc receptors (FcRs) (e.g., Natural Killer (NK) cells, neutrophils, and macrophages) recognize bound antibody on a target cell and subsequently cause lysis of the target cell. The IgG1 subclass binds with high affinity to the Fc receptor and contributes to ADCC while IgG4 binds only weakly. The relative inability of IgG4 to activate effector functions may be desirable under certain circumstances.

Furthermore, the binding site for the FcRn scavenger receptor is present in IgG4 and IgG1 isotypes and both have similar binding characteristics. Therefore, the pharmacokinetics of the IgG1 and IgG4 mimetibodies of the invention are expected to be similar.

The hinge-$C_H2$-$C_H3$ portion of the immunoglobulin region (Hg-$C_H2$-$C_H3$) may also be extensively modified to form variants in accordance with the invention. For example, one or more native sites that provide structural features or functional activity not required by the mimetibody molecules could be removed. These sites may be removed by, for example, substituting or deleting residues, inserting residues into the site or truncating portions containing the site. Exemplary Hg-$C_H2$-$C_H3$ variants are discussed below.

1. Sites involved in disulfide bond formation can be removed by deletion or substitution with other amino acids in the mimetibodies of the invention. Typically, the cysteine residues present in these motifs are removed or substituted. Removal of these sites may avoid disulfide bonding with other cysteine-containing proteins present in the mimetibody-producing host cell or intra-heavy chain disulfide bonding in IgG4-based constructs while still allowing for a dimeric $C_H3$-$C_H2$-hinge domain that is held together non-covalently.

Most IgG type antibodies, such as IgG1, are homodimeric molecules made up of two identical heavy (H) chains and two identical light (L) chains, typically abbreviated $H_2L_2$. Thus, these molecules are generally bivalent with respect to antigen binding, i.e., both antigen binding (Fab) arms of the IgG molecule have identical binding specificity.

IgG4 isotype heavy chains contain a CPSC (SEQ ID NO: 28) motif in their hinge regions capable of forming either inter- or intra-heavy chain disulfide bonds, i.e., the two Cys residues in the CPSC motif may disulfide bond with the corresponding Cys residues in the other heavy chain (inter) or the two Cys residues within a given CPSC motif may disulfide bond with each other (intra). It is believed that in vivo isomerase enzymes are capable of converting inter-heavy chain bonds of IgG4 molecules to intra-heavy chain bonds and vice versa (Aalberse and Schuurman, *Immunology* 105: 9-19 (2002)). Accordingly, since the heavy chain/light chain (HL) pairs in those IgG4 molecules with intra-heavy chain bonds in the hinge region are not covalently associated with each other, they may dissociate into HL monomers that then reassociate with HL monomers derived from other IgG4 molecules forming bispecific, heterodimeric IgG4 molecules. In a bispecific IgG antibody the two Fabs of the antibody molecule differ in the epitopes that they bind. Substituting Ser228 in the hinge region of IgG4 with Pro (S228P) results in "IgG1-like behavior," i.e., the molecules form stable disulfide bonds between heavy chains and therefore, are not susceptible to HL exchange with other IgG4 molecules.

2. The Hg-$C_H2$-$C_H3$ can be modified to make the mimetibodies of the invention more compatible with a selected host cell. For example, when a mimetibody of the invention is expressed recombinantly in a bacterial cell such as *E. coli*, the Pro-Ala sequence in the hinge may be removed to prevent digestion by the *E coli* enzyme proline iminopeptidase.

3. A portion of the hinge region can be deleted or substituted with other amino acids in the mimetibodies of the invention to prevent heterogeneity in the products expressed in a selected host cell.

4. One or more glycosylation sites can be removed in the mimetibodies of the invention. Residues that are typically glycosylated (e.g., Asn) may confer an Fc-dependent, cell-mediated cytolytic activity to the mimetibody. Such residues may be deleted or substituted with residues that are not glycosylated such as Ala.

5. Sites involved in interaction with complement, such as the C1q binding site, can be removed in the mimetibodies of the invention.

6. Sites can be removed that affect binding to Fc receptors other than an FcRn salvage receptor in the mimetibodies of the invention. For example, the Fc receptors involved in ADCC activity can be removed in the mimetibodies of the invention. For example, mutation of Leu234/Leu235 in the hinge region of IgG1 to L234A/L235A or Phe234/Leu235 in the hinge region of IgG4 to P234A/L235A minimizes FcR binding and reduces the ability of the immunoglobulin to mediate complement dependent cytotoxicity and ADCC.

The polypeptides of the invention can also be post-translationally modified by processes such as glycosylation, isomerization, aglycosylation or non-naturally occurring covalent modification such as the addition of polyethylene glycol moieties (pegylation) and lipidation. Such modifications may occur in vivo or in vitro.

Nucleic Acids, Vectors and Cell Lines

Another aspect of the present invention is an isolated polynucleotide encoding at least one HIV gp41 mimetibody polypeptide or a complementary nucleic acid. Other polynucleotides within the scope of the invention are those which, given the degeneracy of the genetic code or codon preferences in a given expression system, encode the polypeptides of the invention.

In one embodiment, the polynucleotides of the invention encode polypeptides having amino acid sequences identical to or substantially homologous to any one of SEQ ID NOs: 1 and 5 to 13. An exemplary polynucleotide has the sequence shown in SEQ ID NO: 2.

Other aspects of the present invention include recombinant vectors comprising at least one HIV gp41 mimetibody encoding polynucleotide. These vectors are useful for expressing HIV gp41 mimetibodies in an appropriate cell line. Vectors within the scope of the invention provide necessary elements for eukaryotic expression, including viral promoter driven vectors, such as CMV promoter driven vectors, e.g., pcDNA3.1, pCEP4 and their derivatives, Baculovirus expression vectors, Drosophila expression vectors and expression vectors that are driven by mammalian gene promoters, such as human Ig gene promoters. Other examples include prokaryotic expression vectors, such as T7 promoter driven vectors, e.g., pET41, lactose promoter driven vectors and arabinose gene promoter driven vectors.

The present invention also relates to cell lines expressing HIV gp41 mimetibodies. The host cells can be prokaryotic or eukaryotic cells, including plant cells. Exemplary eukaryotic cells are mammalian cells, such as but not limited to, COS-1, COS-7, HEK293, BHK21, CHO, BSC-1, HepG2, 653, SP2/0, NS0, 293, HeLa, myeloma, lymphoma cells and plant cells of the genus *Lemna* (duckweed), or any derivative thereof. HEK293, NS0, SP2/0, CHO and *Lemna* cells are particularly useful. The cell lines of the present invention may stably express at least one HIV gp41 mimetibody. The cell lines may be generated by stable or transient transfection procedures that are well known in the art.

The present invention further provides methods for expressing at least one HIV gp41 mimetibody comprising culturing the cell lines under conditions wherein the mimetibody is expressed in detectable or recoverable amounts. The present invention also provides methods for generating at least one HIV gp41 mimetibody comprising translating the mimetibody encoding nucleic acids under conditions in vitro, such that the mimetibody is expressed in detectable or recoverable amounts. The present invention also encompasses HIV gp41 mimetibodies produced by the above methods.

An HIV gp41 mimetibody can be recovered and purified by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylatpatite chromatography and lectin chromatography. High performance liquid chroatography (HPLC) can also be employed for purification.

Methods of Use

The HIV gp41 mimetibodies are useful as, inter alia, research reagents and therapeutic agents. The present invention includes HIV gp41 mimetibodies that are capable of blocking or reducing the fusion of HIV and a host cell membrane. These HIV gp41 mimetibodies of the present invention are useful in treating disorders or symptoms resulting from HIV infection, such as, but not limited to AIDS, opportunistic infections such as Pneumocystis pneumonia, CMV retinitis, Kaposi's saracoma, progressive multifocal leukoencephalopathy (PML), Entameoba diarrhea or other conditions, for example, cachexia or dementia.

Thus, in another aspect, the present invention relates to a method of reducing or blocking the fusion of of HIV and a host cell membrane by administration of an HIV gp41 mimetibody to the host. In particular, the HIV gp41 mimetibody may function as an antagonist of gp41. The term "antagonist" is used in the broadest sense and includes a molecule that is capable of, directly or indirectly, partially or fully counteracting, reducing or inhibiting one or more biological activities of gp41.

The present invention further provides methods for reducing the symptoms of, or treating at least one HIV infection related condition or disease comprising administering a therapeutically effective amount of at least one HIV mimetibody pharmaceutical composition to a patient in need thereof. Further, the mimetibodies of the invention are useful in methods for preventing HIV infection and in methods for post-exposure prophylaxis, i.e., preventing HIV infection sequelae in asymptomatic HIV-positive patients.

As described further below, the pharmaceutical compositions of the invention comprise an effective amount of at least one HIV gp41 mimetibody and a pharmaceutically acceptable carrier or diluent. The effective amount for a given therapy, whether curative or preventative, will generally depend upon many different factors, including means of administration, target site and other medicants administered. Thus, treatment doses will need to be titrated to optimize safety and efficacy.

The methods of the present invention can further comprise co-administration or combination therapies with any other antiretroviral compound, protein or composition such as, for example, the nucleoside analog reverse transcriptase inhibitors zidovudine, didanosine, zalcitabine, stavudine and lamivudine, non-nucleoside reverse transcriptase inhibitors such as nevirapine and delavirdine and protease inhibitors such as saquinavir, ritonavir, indinavir and nelfinavir.

The mode of administration can be any suitable route to deliver the pharmaceutically effective amount of HIV mimetibody of the present invention to a host. For example, the HIV mimetibody can be delivered via parenteral administration, such as subcutaneous, intramuscular, intradermal, intravenous or intranasal administration, or any other suitable means known in the art. Other administration routes that can provide extended delivery and biologically effective concentrations can be accomplished by techniques such as depot formulations and internal or external devices.

Accordingly, another aspect of the present invention is pharmaceutical compositions comprising at least one HIV gp41 mimetibody and a pharmaceutically acceptable carrier or diluent known in the art. The carrier or diluent can be a powder, solution, suspension, emulsion, or colloid.

An HIV mimetibody of the invention is formulated as a pharmaceutical composition in a therapeutically or prophylactically effective amount. The term "effective amount" generally refers to the quantities of mimetibody necessary for effective therapy, i.e., the partial or complete alleviation of the symptom or disorder for which treatment was sought. Included within the definition of effective therapy are prophylactic treatments intended to reduce the likelihood of onset of the above-described symptoms or disorders.

The composition can optionally comprise at least one other antiretroviral compound, protein or composition useful for treating HIV infection or its sequelae. Such additional antiretroviral compound, protein or composition may be directed at distinct steps of viral entry process, for example, CD4 cell binding, co-receptor binding, viral fusion or target other mechanisms of HIV infections such as the HIV reverse transcriptase or protease enzymes. The combination treatment regime is likely to yield potent suppression of viral replication.

The present invention is further described with reference to the following examples. These examples are merely to illustrate aspects of the present invention and are not intended as limitations of this invention.

EXAMPLE 1

Cloning, Expression and Purification of an HIV gp41 Mimetibody in Mammalian Cells T-1249 encoding cDNA was amplified by overlap PCR and inserted into a pCEP4-derived human IgG1 expression vector. pCEP4 was obtained from Invitrogen Corporation, Carlsbad, Calif. The vector contains a CMV promotor, the Epstein Barr Virus (EBV) origin of replication (oriP) and nuclear antigen (EBNA-1) to allow high-copy episomal replication. The vector also supplies sequences encoding other mimetibody components, such as the partial V regions, at least partial hinge region and human IgG1 $C_H2$ and $C_H3$ regions.

The T-1249 mimetibody expression plasmid was transiently transfected into HEK293E cells and the expressed mimetibody was purified from cell culture supernatant using protein A affinity chromatography according to standard procedures.

EXAMPLE 2

Inhibitory Effect of HIV gp41 Mimetibody on HIV Infection

The LTR-Luc assay is based upon HIV Tat protein-mediated transactivation of an HIV LTR linked to a luciferase reporter gene present in a target cell. The binding of Tat to the TAR element in the LTR results in transcriptional activation of luciferase gene expression. Luciferase output is proportional to the amount of HIV infection.

The HIV-1$_{IIIB}$ concentrated virus (Advanced Biotechnologies Inc., Columbia, Md.) was used to infect MT4 cells and generate a working stock of HIV. To generate stable MT4-Luc cells, a luciferase reporter gene under the control of the HIV LTR was transfected into the parental MT4 cell line according to standard procedures known in the art. T-1249 peptide, WQEWEQKITALLEQA-QIQQEKNEYELQKLDKWASLWEWF (SEQ ID NO: 4), was chemically synthesized to approximately 95% purity.

To perform the HIV LTR-Luc assay in a 96-well format, $2 \times 10^4$ MT4-Luc cells were plated in each well. HIV-1 virus and T-1249 peptide (SEQ ID NO: 4) or T-1249 mimetibody (SEQ ID NO: 1) were added per well to a final volume of 200 μl. Samples were run in triplicate during a 4-day assay. At the end of each experiment, Steady-Glo reagent (Promega, Madison, Wis.) was used to detect luciferase activity according to the manufacturer's protocol. Luciferase activity was measured on the BMG FluoStar system (BMG Labtechnologies GmbH, Offenburg, Germany) using the luminescence mode.

Figure 1A:
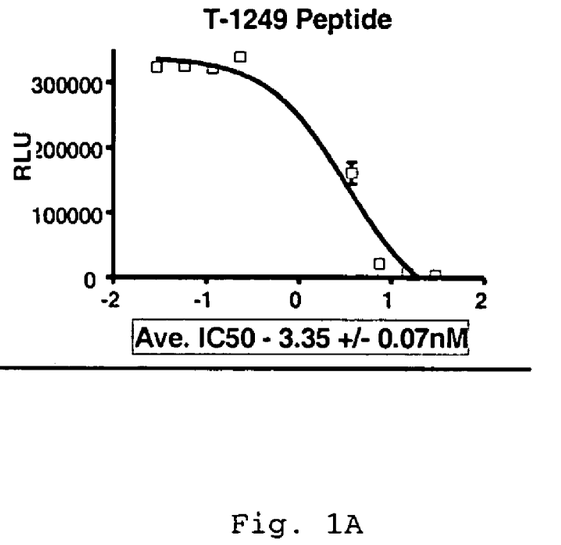
Figure 1B:
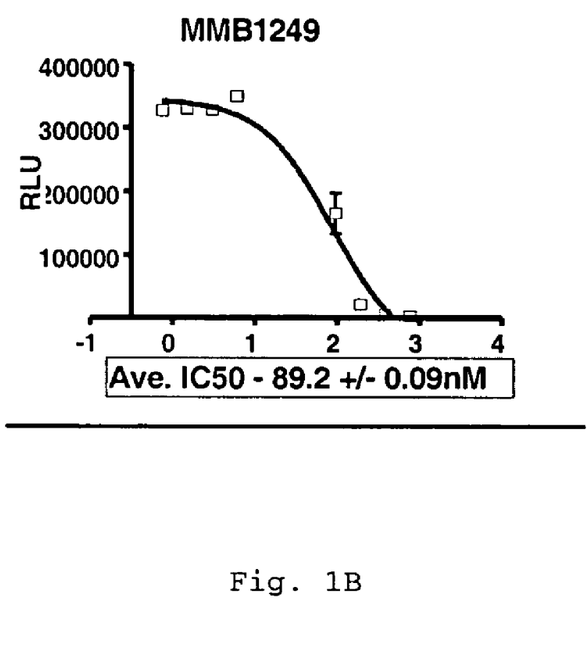

When 50 μl of working viral stock was used, T-1249 peptide was shown to effectively inhibit the HIV infection as reflected in decreased luciferase production (FIG. 1A). The $IC_{50}$ of the peptide was calculated to be ~3.3 nM. In comparison, T-1249 mimetibody retained the inhibitory activity of the peptide (FIG. 1B), although it was not as potent as that of the native peptide. The $IC_{50}$ of the mimetibody was calculated to be ~89 nM.

In similar experiments, the T-1249 mimetibody was also active against other isolates of HIV including an enfuvirtide-resistant strain.

EXAMPLE 3

In Vitro Stability of an HIV gp41 Mimetibody

The stability of the T-1249 mimetibody in vitro was determined using HPLC. The T-1249 mimetibody (SEQ ID NO: 1) was spiked into human serum at 1 mg/ml. Using a C18 chromatography matrix, a peak corresponding to the T-1249 mimetibody was resolved from other serum proteins. The peak identity was confirmed as T-1249 mimetibody using mass spectroscopy and Western blotting. Samples were taken at 0, 5, 25, and 72 hours after the addition of the T-1249 mimetibody into human serum. A background peak was used as a reference for each sample. Using this method, it was found that more than 93% of the T-1249 mimetibody remained intact after 72 hours at 37° C. Similar results were obtained after incubation of the T-1249 mimetibody in either whole heparinized human or cynomologous monkey blood for 24 hours at 37° C.

The present invention now being fully described, it will be apparent to one of ordinary skill in the art that many changes and modifications can be made thereto without departing from the spirit or scope of the appended claims.

The invention claimed is:

1. A polypeptide having an amino acid sequence shown in SEQ ID NO: 1.

2. The polypeptide of claim 1, wherein the polypeptide is post-translationally modified.

3. The polypeptide of claim 2 modified by the addition of polyethylene glycol moieties.

4. A cell line expressing the polypeptide of claim 1.

5. The cell line of claim 4 wherein the cell line is HEK293, NS0, SP2/0, CHO or Lemna cells.

6. A pharmaceutical composition comprising an effective amount of at least one polypeptide as in claim 1 and a pharmaceutically acceptable carrier or diluent.

* * * * *

SEQUENCE LISTING

```
<160> NUMBER OF SEQ ID NOS: 28

<210> SEQ ID NO 1
<211> LENGTH: 288
<212> TYPE: PRT
<213> ORGANISM: Artificial
<220> FEATURE:
<223> OTHER INFORMATION: mimetibody polypeptide

<400> SEQUENCE: 1

Gln Ile Gln Trp Gln Glu Trp Glu Gln Lys Ile Thr Ala Leu Leu Glu
1               5                   10                  15

Gln Ala Gln Ile Gln Gln Glu Lys Asn Glu Tyr Glu Leu Gln Lys Leu
            20                  25                  30

Asp Lys Trp Ala Ser Leu Trp Glu Trp Phe Gly Ser Gly Gly Gly Ser
        35                  40                  45

Gly Thr Leu Val Thr Val Ser Ser Glu Pro Lys Ser Cys Asp Lys Thr
    50                  55                  60

His Thr Cys Pro Pro Cys Pro Ala Pro Glu Leu Leu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
            100                 105                 110

Glu Val Lys Phe Asn Trp Tyr Val Asp Gly Val Glu Val His Asn Ala
        115                 120                 125

Lys Thr Lys Pro Arg Glu Glu Gln Tyr Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Asp Glu Leu Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
        275                 280                 285
```

<210> SEQ ID NO 2
<211> LENGTH: 867
<212> TYPE: DNA
<213> ORGANISM: Artificial
<220> FEATURE:
<223> OTHER INFORMATION: mimetibody DNA

<400> SEQUENCE: 2

```
cagatccagt ggcaggaatg ggaacagaaa attaccgcgc tgctggaaca ggcgcagatt      60
cagcaggaaa aaaacgaata tgaactgcag aaactggata atgggcgag cctgtgggaa      120 tggtttggat ccggtggagg ctccggtacc ttagtcaccg tctcctcaga gcccaaatct     180
tgtgacaaaa ctcacacgtg cccaccgtgc ccagcacctg aactcctggg gggaccgtca     240
gtcttcctct tccccccaaa acccaaggac accctcatga tctcccggac ccctgaggtc     300
acatgcgtgg tggtggacgt gagccacgaa gaccctgagg tcaagttcaa ctggtacgtg     360
gacggcgtgg aggtgcataa tgccaagaca agccgcggg aggagcagta caacagcacg      420
taccgggtgg tcagcgtcct caccgtcctg caccaggact ggctgaatgg caaggagtac     480
aagtgcaagg tctccaacaa agccctccca gcccccatcg agaaaaccat ctccaaagcc     540
aaagggcagc cccgagaacc acaggtgtac accctgcccc catcccggga tgagctgacc     600
aagaaccagg tcagcctgac ctgcctggtc aaaggcttct atcccagcga catcgccgtg     660
gagtgggaga gcaatgggca gccggagaac aactacaaga ccacgcctcc cgtgctggac     720
tccgacggct ccttcttcct ctacagcaag ctcaccgtgg acaagagcag gtggcagcag     780
gggaacgtct tctcatgctc cgtgatgcat gaggctctgc acaaccacta cacgcagaag     840
agcctctccc tgtctccggg taaatga                                          867
```

<210> SEQ ID NO 3
<211> LENGTH: 36
<212> TYPE: PRT
<213> ORGANISM: Artificial
<220> FEATURE:
<223> OTHER INFORMATION: T-20 polypeptide

<400> SEQUENCE: 3

```
Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35
```

<210> SEQ ID NO 4
<211> LENGTH: 39
<212> TYPE: PRT
<213> ORGANISM: Artificial
<220> FEATURE:
<223> OTHER INFORMATION: T-1249 polypeptide

<400> SEQUENCE: 4

```
Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35
```

```
<210> SEQ ID NO 5
<211> LENGTH: 73
<212> TYPE: PRT
<213> ORGANISM: Artificial
<220> FEATURE:
<223> OTHER INFORMATION: mimetibody polypeptide

<400> SEQUENCE: 5

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe Gly Ser Gly Gly Ser Gly Thr Leu
        35                  40                  45

Val Thr Val Ser Ser Glu Pro Lys Ser Cys Asp Lys Thr His Thr Cys
    50                  55                  60

Pro Pro Cys Pro Ala Pro Glu Leu Leu
65                  70

<210> SEQ ID NO 6
<211> LENGTH: 56
<212> TYPE: PRT
<213> ORGANISM: Artificial
<220> FEATURE:
<223> OTHER INFORMATION: mimetibody polypeptide

<400> SEQUENCE: 6

Gln Ile Gln Trp Gln Glu Trp Glu Gln Lys Ile Thr Ala Leu Leu Glu
1               5                   10                  15

Gln Ala Gln Ile Gln Gln Glu Lys Asn Glu Tyr Glu Leu Gln Lys Leu
            20                  25                  30

Asp Lys Trp Ala Ser Leu Trp Glu Trp Phe Gly Gly Ser Cys Pro
        35                  40                  45

Pro Cys Pro Ala Pro Glu Leu Leu
    50                  55

<210> SEQ ID NO 7
<211> LENGTH: 64
<212> TYPE: PRT
<213> ORGANISM: Artificial
<220> FEATURE:
<223> OTHER INFORMATION: mimetibody polypeptide

<400> SEQUENCE: 7

Gln Ile Gln Trp Gln Glu Trp Glu Gln Lys Ile Thr Ala Leu Leu Glu
1               5                   10                  15

Gln Ala Gln Ile Gln Gln Glu Lys Asn Glu Tyr Glu Leu Gln Lys Leu
            20                  25                  30

Asp Lys Trp Ala Ser Leu Trp Glu Trp Phe Gly Gly Gly Ser Gly Gly
        35                  40                  45

Gly Ser Gly Gly Gly Ser Cys Pro Pro Cys Pro Ala Pro Glu Leu Leu
    50                  55                  60

<210> SEQ ID NO 8
<211> LENGTH: 74
<212> TYPE: PRT
<213> ORGANISM: Artificial
<220> FEATURE:
<223> OTHER INFORMATION: mimetibody polypeptide

<400> SEQUENCE: 8

Gln Ile Gln Trp Gln Glu Trp Glu Gln Lys Ile Thr Ala Leu Leu Glu
```

```
                  1               5                  10                 15
Gln Ala Gln Ile Gln Gln Glu Lys Asn Glu Tyr Glu Leu Gln Lys Leu
                 20                 25                 30

Asp Lys Trp Ala Ser Leu Trp Glu Trp Phe Gly Ser Gly Gly Ser
             35                 40                 45

Gly Gly Gly Ser Gly Gly Gly Ser Gly Gly Ser Gly Gly Gly Ser
         50                 55                 60

Cys Pro Pro Cys Pro Ala Pro Glu Leu Leu
65                  70

<210> SEQ ID NO 9
<211> LENGTH: 52
<212> TYPE: PRT
<213> ORGANISM: Artificial
<220> FEATURE:
<223> OTHER INFORMATION: mimetibody polypeptide

<400> SEQUENCE: 9

Gly Gly Gly Ser Gly Gly Gly Ser Gly Gly Gly Ser Trp Gln Glu
1               5                  10                 15

Trp Glu Gln Lys Ile Thr Ala Leu Leu Glu Gln Ala Gln Ile Gln Gln
                 20                 25                 30

Glu Lys Asn Glu Tyr Glu Leu Gln Lys Leu Asp Lys Trp Ala Ser Leu
             35                 40                 45

Trp Glu Trp Phe
         50

<210> SEQ ID NO 10
<211> LENGTH: 73
<212> TYPE: PRT
<213> ORGANISM: Artificial
<220> FEATURE:
<223> OTHER INFORMATION: mimetibody polypeptide

<400> SEQUENCE: 10

Gln Ile Gln Tyr Thr Ser Leu Ile His Ser Leu Ile Glu Glu Ser Gln
1               5                  10                 15

Asn Gln Gln Glu Lys Asn Glu Gln Glu Leu Leu Glu Leu Asp Lys Trp
                 20                 25                 30

Ala Ser Leu Trp Asn Trp Phe Gly Ser Gly Gly Gly Ser Gly Thr Leu
             35                 40                 45

Val Thr Val Ser Ser Glu Pro Lys Ser Cys Asp Lys Thr His Thr Cys
         50                 55                 60

Pro Pro Cys Pro Ala Pro Glu Leu Leu
65                  70

<210> SEQ ID NO 11
<211> LENGTH: 285
<212> TYPE: PRT
<213> ORGANISM: Artificial
<220> FEATURE:
<223> OTHER INFORMATION: mimetibody polypeptide

<400> SEQUENCE: 11

Gln Ile Gln Tyr Thr Ser Ile Ile Tyr Thr Leu Leu Glu Glu Ser Gln
1               5                  10                 15

Asn Gln Gln Glu Lys Asn Glu Gln Glu Leu Leu Glu Leu Asp Lys Trp
                 20                 25                 30

Ala Ser Leu Trp Asn Trp Phe Gly Ser Gly Gly Gly Ser Gly Thr Leu
             35                 40                 45
```

```
Val Thr Val Ser Ser Glu Pro Lys Ser Cys Asp Lys Thr His Thr Cys
        50                  55                  60
Pro Pro Cys Pro Ala Pro Glu Leu Leu Gly Gly Pro Ser Val Phe Leu
 65                  70                  75                  80
Phe Pro Pro Lys Pro Lys Asp Thr Leu Met Ile Ser Arg Thr Pro Glu
                 85                  90                  95
Val Thr Cys Val Val Val Asp Val Ser His Glu Asp Pro Glu Val Lys
                100                 105                 110
Phe Asn Trp Tyr Val Asp Gly Val Glu Val His Asn Ala Lys Thr Lys
                115                 120                 125
Pro Arg Glu Glu Gln Tyr Asn Ser Thr Tyr Arg Val Val Ser Val Leu
            130                 135                 140
Thr Val Leu His Gln Asp Trp Leu Asn Gly Lys Glu Tyr Lys Cys Lys
145                 150                 155                 160
Val Ser Asn Lys Ala Leu Pro Ala Pro Ile Glu Lys Thr Ile Ser Lys
                165                 170                 175
Ala Lys Gly Gln Pro Arg Glu Pro Gln Val Tyr Thr Leu Pro Pro Ser
                180                 185                 190
Arg Asp Glu Leu Thr Lys Asn Gln Val Ser Leu Thr Cys Leu Val Lys
            195                 200                 205
Gly Phe Tyr Pro Ser Asp Ile Ala Val Glu Trp Glu Ser Asn Gly Gln
210                 215                 220
Pro Glu Asn Asn Tyr Lys Thr Thr Pro Pro Val Leu Asp Ser Asp Gly
225                 230                 235                 240
Ser Phe Phe Leu Tyr Ser Lys Leu Thr Val Asp Lys Ser Arg Trp Gln
                245                 250                 255
Gln Gly Asn Val Phe Ser Cys Ser Val Met His Glu Ala Leu His Asn
                260                 265                 270
His Tyr Thr Gln Lys Ser Leu Ser Leu Ser Pro Gly Lys
            275                 280                 285

<210> SEQ ID NO 12
<211> LENGTH: 70
<212> TYPE: PRT
<213> ORGANISM: Artificial
<220> FEATURE:
<223> OTHER INFORMATION: mimetibody polypeptide

<400> SEQUENCE: 12

Tyr Thr Ser Leu Ile His Ser Leu Ile Glu Glu Ser Gln Asn Gln Gln
 1               5                  10                  15
Glu Lys Asn Glu Gln Glu Leu Leu Glu Leu Asp Lys Trp Ala Ser Leu
             20                  25                  30
Trp Asn Trp Phe Gly Ser Gly Gly Ser Gly Thr Leu Val Thr Val
             35                  40                  45
Ser Ser Glu Pro Lys Ser Cys Asp Lys Thr His Thr Cys Pro Pro Cys
         50                  55                  60
Pro Ala Pro Glu Leu Leu
 65                  70

<210> SEQ ID NO 13
<211> LENGTH: 70
<212> TYPE: PRT
<213> ORGANISM: Artificial
<220> FEATURE:
<223> OTHER INFORMATION: mimetibody polypeptide
```

```
<400> SEQUENCE: 13

Tyr Thr Ser Ile Ile Tyr Thr Leu Leu Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe Gly Ser Gly Gly Gly Ser Gly Thr Leu Val Thr Val
                35                  40                  45

Ser Ser Glu Pro Lys Ser Cys Asp Lys Thr His Thr Cys Pro Pro Cys
    50                  55                  60

Pro Ala Pro Glu Leu Leu
65                  70

<210> SEQ ID NO 14
<211> LENGTH: 4
<212> TYPE: PRT
<213> ORGANISM: Artificial
<220> FEATURE:
<223> OTHER INFORMATION: linker peptide

<400> SEQUENCE: 14

Gly Gly Gly Ser
1

<210> SEQ ID NO 15
<211> LENGTH: 6
<212> TYPE: PRT
<213> ORGANISM: Artificial
<220> FEATURE:
<223> OTHER INFORMATION: linker peptide

<400> SEQUENCE: 15

Gly Ser Gly Gly Gly Ser
1               5

<210> SEQ ID NO 16
<211> LENGTH: 8
<212> TYPE: PRT
<213> ORGANISM: Homo sapiens

<400> SEQUENCE: 16

Gly Thr Leu Val Thr Val Ser Ser
1               5

<210> SEQ ID NO 17
<211> LENGTH: 15
<212> TYPE: PRT
<213> ORGANISM: Homo sapiens

<400> SEQUENCE: 17

Glu Pro Lys Ser Cys Asp Lys Thr His Thr Cys Pro Pro Cys Pro
1               5                   10                  15

<210> SEQ ID NO 18
<211> LENGTH: 15
<212> TYPE: PRT
<213> ORGANISM: Artificial
<220> FEATURE:
<223> OTHER INFORMATION: V2 variant

<400> SEQUENCE: 18

Glu Pro Lys Ser Ala Asp Lys Thr His Thr Cys Pro Pro Cys Pro
1               5                   10                  15
```

```
<210> SEQ ID NO 19
<211> LENGTH: 12
<212> TYPE: PRT
<213> ORGANISM: Homo sapiens

<400> SEQUENCE: 19

Glu Ser Lys Tyr Gly Pro Pro Cys Pro Ser Cys Pro
1               5                   10

<210> SEQ ID NO 20
<211> LENGTH: 12
<212> TYPE: PRT
<213> ORGANISM: Artificial
<220> FEATURE:
<223> OTHER INFORMATION: hinge variant

<400> SEQUENCE: 20

Glu Ser Lys Tyr Gly Pro Pro Cys Pro Pro Cys Pro
1               5                   10

<210> SEQ ID NO 21
<211> LENGTH: 5
<212> TYPE: PRT
<213> ORGANISM: Homo sapiens

<400> SEQUENCE: 21

Cys Pro Pro Cys Pro
1               5

<210> SEQ ID NO 22
<211> LENGTH: 110
<212> TYPE: PRT
<213> ORGANISM: Homo sapiens

<400> SEQUENCE: 22

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 23
<211> LENGTH: 110
<212> TYPE: PRT
<213> ORGANISM: Artificial
<220> FEATURE:
<223> OTHER INFORMATION: engineered G1 CH2

<400> SEQUENCE: 23

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

```
Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
             85                  90                  95

Ala Leu Pro Ala Pro Ile Glu Lys Thr Ile Ser Lys Ala Lys
        100                 105                 110
```

<210> SEQ ID NO 24
<211> LENGTH: 110
<212> TYPE: PRT
<213> ORGANISM: Homo sapiens

<400> SEQUENCE: 24

```
Ala Pro Glu Phe Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser Gln Glu Asp Pro Glu Val Gln Phe Asn Trp Tyr
         35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
             85                  90                  95

Gly Leu Pro Ser Ser Ile Glu Lys Thr Ile Ser Lys Ala Lys
        100                 105                 110
```

<210> SEQ ID NO 25
<211> LENGTH: 110
<212> TYPE: PRT
<213> ORGANISM: Artificial
<220> FEATURE:
<223> OTHER INFORMATION: engineered G4 CH2

<400> SEQUENCE: 25

```
Ala Pro Glu Ala Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser Gln Glu Asp Pro Glu Val Gln Phe Asn Trp Tyr
         35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
             85                  90                  95

Gly Leu Pro Ser Ser Ile Glu Lys Thr Ile Ser Lys Ala Lys
        100                 105                 110
```

<210> SEQ ID NO 26
<211> LENGTH: 107
<212> TYPE: PRT

```
<213> ORGANISM: Homo sapiens

<400> SEQUENCE: 26

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 27
<211> LENGTH: 107
<212> TYPE: PRT
<213> ORGANISM: Homo sapiens

<400> SEQUENCE: 27

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 28
<211> LENGTH: 4
<212> TYPE: PRT
<213> ORGANISM: Homo sapiens

<400> SEQUENCE: 28

Cys Pro Ser Cys
1
```